United States Patent [19]
Seino

[11] Patent Number: 4,780,541
[45] Date of Patent: Oct. 25, 1988

[54] METHOD FOR PREPARING 2-PHENYLBENZOTRIAZOLES AND 2-PHENYLBENZOTRIAZOLE-N-OXIDES

[75] Inventor: Shuichi Seino, Kobe, Japan

[73] Assignee: Chemipro Kasei Kaisha, Ltd., Hyogo, Japan

[21] Appl. No.: 906,147

[22] Filed: Sep. 11, 1986

[51] Int. Cl.[4] .............................................. C07D 249/20
[52] U.S. Cl. .................................. 548/260; 548/257; 548/261
[58] Field of Search ........................ 548/257, 260, 261

[56] References Cited

U.S. PATENT DOCUMENTS 4,642,350  2/1987  Davatz ................................ 548/260

FOREIGN PATENT DOCUMENTS 167976  10/1982  Japan .................................... 548/260

OTHER PUBLICATIONS

Fieser and Fieser, *Organic Chemistry*, 3rd Ed. (1956: Reinhold Publishing Co., New York), pp. 350 and 362.
March, J., *Advanced Organic Chemistry*, 2nd Ed. (1977: McGraw-Hill Book Co., New York), p. 1138.

*Primary Examiner*—Donald G. Daus
*Assistant Examiner*—Mark W. Noel
*Attorney, Agent, or Firm*—Felfe & Lynch

[57] ABSTRACT

This invention relates to a method for preparing a 2-phenylbenzotriazole of formula I,

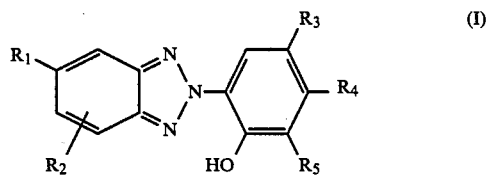

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4), which comprises reducing an o-nitroazobenzene of formula III,

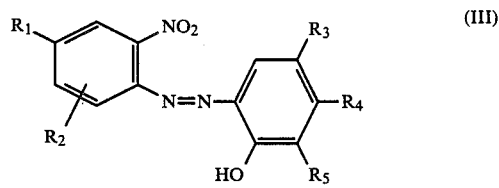

(wherein $R_1$, $R_2$, $R_3$, $R_4$ and $R_5$ are as defined above) with an aldehyde reducing agent in the presence of an aromatic ketone catalyst and base.

This invention further relates to a method for preparing a 2-phenylbenzotriazole of formula I as derfined above, which comprises reducing 1 mole 2-phenylbenzotriazole-N-oxide of formula II,

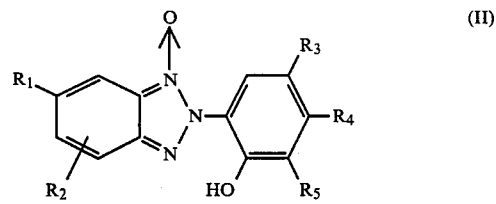

(wherein $R_1$, $R_2$, $R_3$, $R_4$ and $R_5$ are as defined above) with 1 to 4 mole aldehyde in the presence of an aromatic ketone catalyst and base.

This invention still further relates to a method for preparing a 2-phenylbenzotriazole-N-oxide of formula II as defined above, which comprises reducing 1 mole o-nitroazobenzene of formula III as defined above with 1 to 2 mole aldehyde in the presence of an aromatic ketone catalyst and base.

7 Claims, No Drawings

METHOD FOR PREPARING 2-PHENYLBENZOTRIAZOLES AND 2-PHENYLBENZOTRIAZOLE-N-OXIDES

BACKGROUND OF THE INVENTION (a) Field of the Invention

This invention relates to a method for preparing 2-phenylbenzotriazoles having the following general formula I, which are useful as an ultraviolet ray absorber.

This invention further relates to a method for preparing 2-phenylbenzotriazole-N-oxides having the following general formula II, which are a useful intermediate for said 2-phenylbenzotriazoles.

(b) Description of the Prior Art 2-phenylbenzotriazoles having the following general formula I,

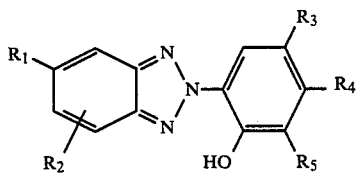

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4) are known to be useful as an ultraviolet ray absorber to be added to plastics, paints, oils and the like.

2-phenylbenzotriazole-N-oxides having the general formula II,

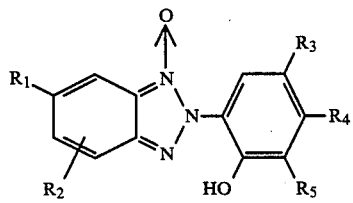

(wherein $R_1$, $R_2$, $R_3$, $R_4$ and $R_5$ are the same as defined above with regard to the general formula I) are known to be an important intermediate for said 2-phenylbenzotriazoles.

Heretofore, these 2-phenylbenzotriazoles and 2-phenylbenzotriazole-N-oxides have been produced by chemically or electrolytically reducing o-nitroazobenzene derivatives having the general formula III,

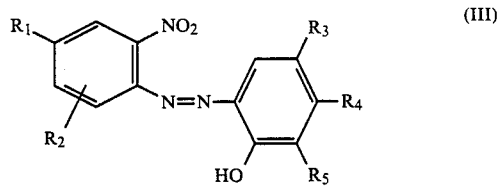

(wherein $R_1$, $R_2$, $R_3$, $R_4$ and $R_5$ are the same as defined above with regard to the general formula I). However, these conventional methods respectively have merits and demerits, and are not always satisfactory.

For example, Japanese Patent Publication No. 37-5934 and U.S. Pat. No. 3,773,751 disclose a method for preparing 2-phenylbenzotriazoles or 2-phenylbenzotriazole-N-oxides by chemically reducing o-nitroazobenzene derivatives in an alcoholic sodium hydroxide solution with zinc powder at a satisfactory yield. However, this sodium hydroxide-zinc system produces zinc sludge which results in waste water contamination problems.

As disclosed in U.S. Pat. No. 2,362,988, ammonium sulfide, alkali-sulfide, zinc-ammonia system, hydrogen sulfide-sodium system and zinc-hydrochloric acid system are used as a chemical reducing agent for the above mentioned reduction reaction. However, this conventional method produces a large amount of sulfite or zinc salts which result in waste water contamination. The sulfite further generates sulfurous acid gas, and the used sulfide type reducing agent generates poisonous hydrogen sulfide, which results in environmental polution problems.

Japanese Patent Laid Open Nos. 51-138679 and 51-138680 disclose a reduction method by the addition of pressurized hydrogen. Japanese Patent Laid Open No. 50-88072 discloses a reduction method by hydrazine. However, these methods are not satisfactory in view of yield and economy, and it is impossible to obtain the desired product of high purity because a side reaction is caused during the main reaction. Particularly, in the case of producing a chlorine-containing product, a side reaction such as dechlorination reaction is caused.

SUMMARY OF THE INVENTION

An object of the present invention is to provide a novel method for preparing 2-phenylbenzotriazoles and 2-phenylbenzotriazole-N-oxides, which solves the above mentioned problems of the conventional methods.

(i) That is, an object of the present invention is to provide a method for preparing 2-phenylbenzotriazoles having the general formula I,

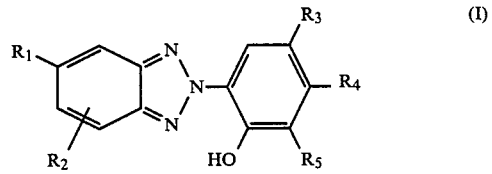

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4), characterized by reducing o-nitroazobenzenes having the general formula III,

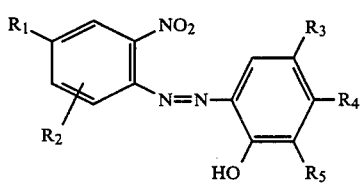

(wherein $R_1$, $R_2$, $R_3$, $R_4$ and $R_5$ are the same as defined above) with an aldehyde catalyst in the presence of an aromatic ketone compound catalyst and base.

(ii) Another object of the present invention is to provide a method for preparing 2-phenylbenzotriazoles having the general formula I,

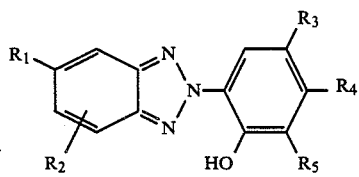

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4), characterized by reducing 2-phenylbenzotriazole-N-oxides having the general formula II,

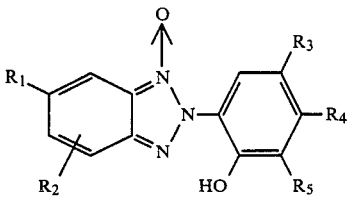

(wherein $R_1$, $R_2$, $R_3$, $R_4$ and $R_5$ are the same as defined above) with an aldehyde reducing agent in an amount of 1 to 4 moles per mole of said 2-phenylbenzotriazole-N-oxides having the general formula II in the presence of an aromatic ketone compound catalyst and base.

(iii) Still other object of the present invention is to provide a method for preparing 2-phenylbenzotriazole-N-oxides having the general formula II,

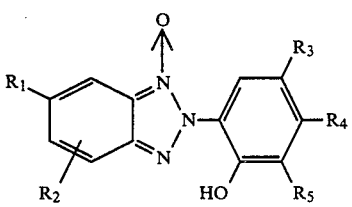

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4), characterized by reducing o-nitroazobenzenes having the general formula III,

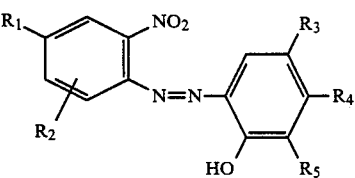

(wherein $R_1$, $R_2$, $R_3$, $R_4$ and $R_5$ are the same as defined above) with an aldehyde reducing agent in an amount of 1 to 2 moles per mole of said o-nitroazobenzenes having the general formula III in the presence of an aromatic ketone compound catalyst and base.

DETAILED DESCRIPTION OF THE INVENTION

In order to solve the above mentioned problems of the conventional methods, I have variously studied and found that the desired 2-phenylbenzotriazoles having the general formula I,

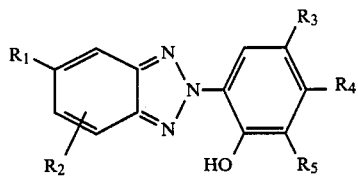

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4) can be produced with technically and economically satisfactory results without causing environmental polution, by reducing (i) o-nitroazobenzenes having the general formula III,

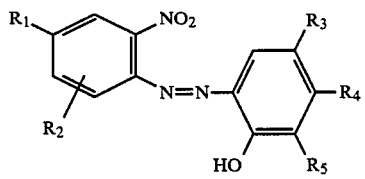

(wherein $R_1$, $R_2$, $R_3$, $R_4$ and $R_5$ are the same as defined above) or (ii) 2-phenylbenzotriazole-N-oxides having the general formula II,

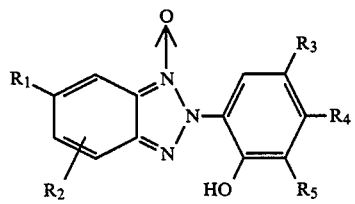

(wherein $R_1$, $R_2$, $R_3$, $R_4$ and $R_5$ are the same as defined above) with an aldehyde reducing agent in the presence of an aromatic ketone compound catalyst and base.

The desired product obtained by the method of the present invention has a higher purity, and accordingly has more favourable thermostability as compared with the product obtained by conventional method.

The method (i) for preparing 2-phenylbenzotriazoles having the general formula I by reducing o-nitroazobenzenes having the general formula III in accordance with the present invention can be carried out by either one step or two steps depending on the conditions of temperature and the amount of aldehydes used as mentioned below.

In the case of one step method:

The suitable temperature condition for this process [Process (a)] is about 20° to 130° C., preferably 40° to 100° C., and an aldehyde reducing agent is suitably used in an amount of about 2 to 4 moles per mole of the starting material, i.e. o-nitroazobenzenes of the general formula III. The reaction is carried out in the following manner.

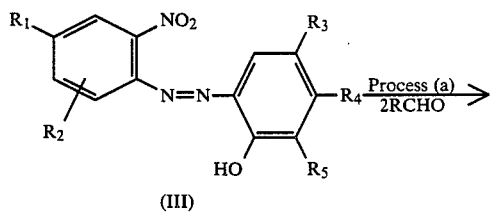

(III)

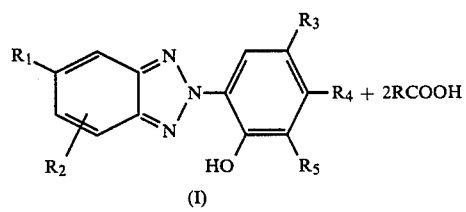

(I)

(wherein $R_1$, $R_2$, $R_3$, $R_4$ and $R_5$ are the same as defined above, and R represents hydrogen, alkyl group, phenyl group or substituted phenyl group). In the case of two step method:

The suitable temperature condition is the same as in the above Process (a), i.e. about 20° to 130° C., preferably about 40° to 100° C. The two step method is sometimes advantageous in view of the quality of product and the yield although it takes two steps. An aldehyde reducing agent is suitably used in an amount of 1 to 2 moles per mole of the starting material, i.e. o-nitroazobenzenes of the general formula III at the first step [Process (b)] to produce an intermediate product, and 1 to 4 moles, preferably 1 to 2 moles per mole of the intermediate, i.e. 2-phenylbenzotriazole-N-oxides of the general formula II at the second step [Process (c)].

The reaction is carried out in the following manner.

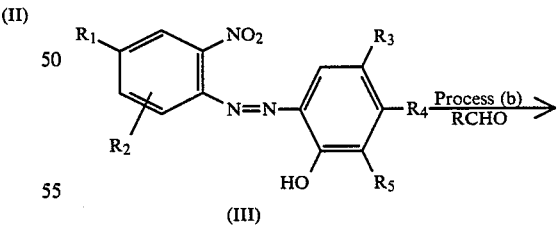

(III)

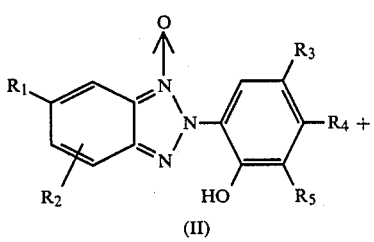

(II)

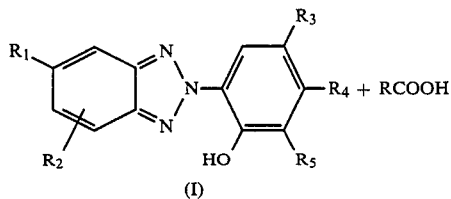

(I)

(wherein $R_1$, $R_2$, $R_3$, $R_4$, $R_5$ and R are the same as defined above).

The method (ii) for preparing 2-phenylbenzotriazoles of the general formula I by reducing 2-phenylbenzotriazole-N-oxides of the general formula II is carried out in quite the same manner as in the above mentioned Process (c).

In the method (ii), the desired 2-phenylbenzotriazole-N-oxides having the general formula II,

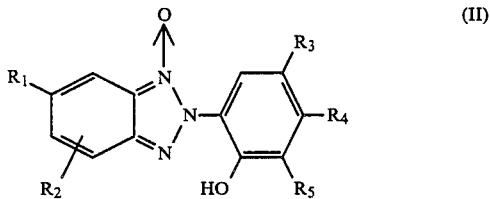

(II)

(wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4) can be produced with technically and economically satisfactory results without causing environmental polution, by reducing o-nitroazobenzenes having the general formula III,

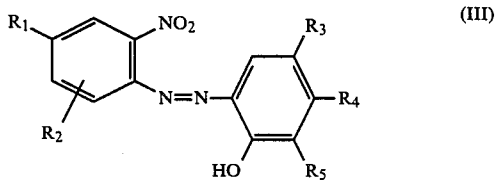

(III)

(wherein $R_1$, $R_2$, $R_3$, $R_4$ and $R_5$ are the same as defined above) with an aldehyde reducing agent in the presence of an aromatic ketone compound catalyst and base.

This reaction of the method (iii) is carried out in the following manner.

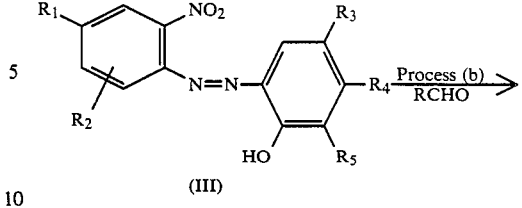

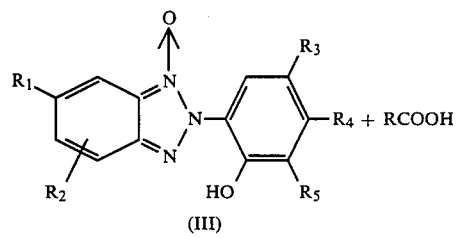

(III)

(wherein $R_1$, $R_2$, $R_3$, $R_4$, $R_5$ and R are the same as defined above).

This reaction is quite the same as that of the above mentioned Process (b). The suitable temperature condition is about 20° to 130° C., preferably about 40° to 100° C., and an aldehyde reducing agent is suitably used in an amount of 1 to 2 moles per mole of the starting material, i.e. o-nitroazobenzenes of the general formula III.

In order to smoothly carry out reaction, all the reactions of the above mentioned Process (a), Process (b) and Process (c) are carried out in an aqueous solution, or in an inert solvent such as alcohols, toluene, acetone, dimethylsulfoxide, acetonitrile and the like, or in a mixture of the above mentioned inert solvent with water. If necessary, a surface active agent, a phase-transfer catalyst, and the like may be added.

Examples of o-nitroazobenzenes expressed by the general formula III used as a starting material in the methods (i) and (iii) include:
2-nitro-2'-hydroxy-5'-methylazobenzene,
2-nitro-2'-hydroxy-5'-t-octylazobenzene,
2-nitro-2'-hydroxy-5'-t-butylazobenzene,
2-nitro-2',4'-dihydroxyazobenzene,
2-nitro-4-chloro-2',4'-dihydroxyazobenzene,
2-nitro-2'-hydroxy-4'-methoxyazobenzene,
2-nitro-2'-hydroxy-5'-t-amylazobenzene,
2-nitro-4'-chloro-2'-hydroxy-5'-t-amylazobenzene,
2-nitro-2'-hydroxy-5'-n-dodecylazobenzene,
2-nitro-4-chloro-2'-hydroxy-5'-n-dodecylazobenzene,
2-nitro-4-chloro-2'-hydroxy-5'-t-octylazobenzene,
2-nitro-4-methyl-2'-hydroxy-5'-methylazobenzene,
2-nitro-4,6-dichloro-2'-hydroxy-5'-t-butylazobenzene, and
2-nitro-4-carboxy-2'-hydroxy-5-methylazobenzene.

Examples of 2-phenylbenzotriazole-N-oxides of the general formula II used in the method (ii) of the present invention include:
2-(2-hydroxy-5-methylphenyl)benzotriazole-N-oxide,
2-(2-hydroxy-5-t-butylphenyl)benzotriazole-N-oxide,
2-(2-hydroxy-5-t-octylphenyl)benzotriazole-N-oxide,
2-(2,4-dihydroxyphenyl)benzotriazole-N-oxide,
2-(2,4'-dihydroxyphenyl)-5-chlorobenzotriazole-N-oxide,
2-(2-hydroxy-4'-methoxyphenyl)benzotriazole-N-oxide,
2-(2-hydroxy-5-t-amylphenyl)benzotriazole-N-oxide,
2-(2-hydroxy-5-n-dodecylphenyl)benzotriazole-N-oxide, 2-(2-hydroxy-5-n-dodecylphenyl)-5-chlorobenzo-
triazole-N-oxide,
2-(2-hydroxy-5-t-octylphenyl)-5-chlorobenzotriazole-
N-oxide,
2-(2-hydroxy-5-methylphenyl)-5-methylbenzotriazole-
N-oxide,
2-(2-hydroxy-5-methylphenyl)-5-carboxybenzotriazole-
N-oxide,
2-(2-hydroxy-3-t-butyl-5-methylphenyl)-5-chloroben-
zotriazole-N-oxide,
2-(2-hydroxy-3,5-di-t-butylphenyl)-5-chlorobenzo-
triazole-N-oxide,
2-(2-hydroxy-3,5-di-t-amylphenyl)benzotriazole-N-
oxide,
2-(2-hydroxy-3,5'-di-t-butylphenyl)benzotriazole-N-
oxide,
2-(2-hydroxy-3-t-butyl-5-methylphenyl)benzotriazole-
N-oxide,
2-(2-hydroxy-3,5'-di-t-octylphenyl)benzotriazole-N-
oxide,
2-(2-hydroxy-3,5'-di-t-octylphenyl)-5-chlorobenzo-
triazole-N-oxide,
2-(2-hydroxy-3-t-butyl-5-methylphenyl)-5-methylben-
zotriazole-N-oxide,
2-(2-hydroxy-3,5'-di-t-butylphenyl)-5-n-butylbenzo-
triazole-N-oxide,
2-(2-hydroxy-3-sec-butyl-5-t-butylphenyl)-5-n-butyl-
benzotriazole-N-oxide,
2-(2-hydroxy-3-sec-butyl-5-t-butylphenyl)-5-t-butylben-
zotriazole-N-oxide,
2-(2-hydroxy-3,5-di-t-butylphenyl)-5,7-dichlorobenzo-
triazole-N-oxide,
2-(2-hydroxy-3,5-di-t-amylphenyl)-5-chlorobenzo-
triazole-N-oxide,
2-[2-hydroxy-3,5-di-($\alpha,\alpha$-dimethylbenzyl)phenyl]ben-
zotriazole-N-oxide,
2-[2-hydroxy-3,5-di-($\alpha,\alpha$-dimethylbenzyl)phenyl]-5-
chlorobenzotriazole-N-oxide,
2-(2-hydroxy-3-$\alpha$-methylbenzyl-5-metylphenyl)benzo-
triazole-N-oxide, and
2-(2-hydroxy-3-$\alpha$-methylbenzyl-5-metylphenyl)-5-
chlorobenzotriazole-N-oxide.

The starting material, i.e. o-nitroazobenzenes of the general formula III used in the present invention can be easily prepared by diazotizing o-nitroanilines expressed by the following general formula IV,

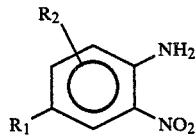

(wherein $R_1$ and $R_2$ are the same as defined above) by the usual method and by subjecting the resultant product to coupling reaction with phenols expressed by the general formula V,

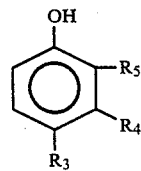

(wherein $R_3$, $R_4$ and $R_5$ are the same as defined above).

It is preferable to prepare these 2-phenyltriazole-N-oxides of the general formula II by reducing o-nitroazobenzenes of the general formula III as a starting material in accordance with the above mentioned Process (b), but these materials can also be prepared by other known methods.

Examples of aldehydes used as a reducing agent include formaldehyde, paraformaldehyde, acetoaldehyde, benzaldehyde, anisaldehyde, and the like. Among them, formaldehyde and paraformaldehyde are most preferable.

These aldehyde reducing agents are used in an amount of 2 to 4 moles per mole of o-nitroazobenzenes of the general formula III when 2-phenylbenzotriazoles of the general formula I are prepared from said o-nitroazobenzenes by one step as shown in the above mentioned Process (a) [Method (i)].

These aldehyde reducing agents are used in an amount of 1 to 4 moles, preferably 1 to 2 moles per mole of 2-phenylbenzotriazole-N-oxides of the general formula II when 2-phenylbenzotriazoles of the general formula I are prepared from said 2-phenylbenzotriazole-N-oxides as shown in the above mentioned Process (c) [Method (ii)].

These aldehyde reducing agents are used in an amount of 1 to 2 moles per mole of o-nitroazobenzenes of the general formula III when 2-phenylbenzotriazole-N-oxides of the general formula II are prepared from said o-nitroazobenzenes as shown in the above mentioned Process (b) [Method (iii)].

Examples of an aromatic ketone compound catalyst include benzophenone; benzophenone substituted with alkyl group, alkoxyl group, halogen atom, or hydroxyl group; benzanthrone; anthrone; 9-fluorenone; 9-xanthenone; and the like. Among them, preferable examples include 9-fluorenone, anthrone and benzanthrone. These aromatic ketone catalysts may be used alone or in a mixture of two or more. It is sometimes more preferable to use them in a mixture of two or more.

In any case of the above mentioned Processes (a), (b) and (c), an aromatic ketone catalyst is used generally in an amount of 0.2 to 30%, preferably 2 to 20% on the basis of the weight of the starting material, i.e. o-nitroazobenzenes or 2-phenylbenzotriazole-N-oxides.

Examples of the base used in the present invention include sodium hydroxide, potassium hydroxide and the like. The base is used in an amount of 1 to 12 moles, preferably 2 to 8 moles per one mole of the starting material, i.e. o-nitroazobenzenes or 2-phenylbenzotriazole-N-oxides.

The present invention is further illustrated by the following Examples, but is not limited thereto.

EXAMPLE 1

2-nitro-2'-hydroxy-5'-methylazobenzene 12.9 g was added to a mixture of methanol 60 ml, water 30 ml and 97% sodium hydroxide 12.4 g, and the resultant mixure was stirred while raising temperature to 65° C. Thereafter, the mixture was cooled to 40° C., and 9-fluorenone 0.8 g and then 80% paraformaldehyde 2.1 g were added to the mixture for 1 hour. The resultant mixture was then heated to the boiling point (75° C.), and was stirred at the boiling point for 6 hours, thus almost all of the azobenzene having disappeared to produce 2-(2-hydroxy-5-methylphenyl)benzotriazole-N-oxide.

Thereafter, water 50 ml was added to the reaction liquor, and the reaction liquor was neutralized to pH 8 with 62% sulfuric acid 16 g to precipitate a crystal. The crystal thus obtained was filtered by suction, and the separated crystal was then dried, thus producing 10.7 g of 2-(2-hydroxy-5-methylphenyl)benzotriazole-N-oxide having a melting point of 138° to 140° C. at the yield of 89.0%.

EXAMPLE 2

The same procedure as in Example 1 was repeated, except that 2-nitro-2'-hydroxy-5'-methylazobenzene 12.9 g was replaced respectively by (a) 2-nitro-2'-hydroxy-5'-butylazobenzene 14.9 g, (b) 2-nitro-2'-hydroxy-5'-t-octylazobenzene 17.8 g, and (c) 2-nitro-2',4'-dihydroxyazobenzene 14.9 g.

The products thus obtained and their properties are as follows:
(a) 2-(2-hydroxy-5-t-butylphenyl)benzotriazole-N-oxide: Yield: 12.7 g (90.0%), Melting Point: 73° to 78° C.
(b) 2-(2-hydroxy-5-t-octylphenyl)benzotriazole-N-oxide: Yield: 14.2 g (84.0%), Melting Point: 106° to 111° C.
(c) 2-(2,4'-dihydroxyphenyl)benzotriazole-N-oxide: Yield: 9.7 g (80.0%), Melting Point: 246° to 248° C.

EXAMPLE 3

95% potassium hydroxide 17.7 g was added and dissolved in a mixture of ethyl alcohol 80 ml and water 10 ml. 2-nitro-2'-hydroxy-5'-methylazobenzene 12.9 g was then added to the resultant solution at 50° to 60° C. for 30 minutes while stirring, and thereafter 9-fluorenone 0.6 g and 35% formalin 5.6 g were added to the solution in 30 minutes. The resultant mixture was stirred for 1 hour at 65° to 70° C., and was further reacted at the boiling point (85° C.) for 4 hours, thus almost all of the azobenzene having disappeared to produce 2-(2-hydroxy-5-methylphenyl)benzotriazole-N-oxide.

Thereafter, water 50 ml was added to the reaction liquor, and the reaction liquor was neutralized to pH 8 with 62% sulfuric acid to precipitate a crystal. The crystal thus obtained was filtered by suction to separate the crystal, and the separated crystal was fully washed with water and further with ethyl alcohol. The washed crystal was then dried, thus producing 10.6 g of 2-(2-hydroxy-5-methylphenyl)benzotriazole-N-oxide having a melting point of 138° to 140° C. at the yield of 88.0%.

EXAMPLE 4

Methanol 60 ml, water 30 ml, 97% sodium hydroxide 12.4 g, and 2-nitro-2'-hydroxy-5'-methylazobenzene 12.9 g were mixed and stirred. After adding benzanthrone 1.2 g to the resultant mixture at 65° to 70° C., 80% paraformaldehyde 2.3 g was added to the mixture for 2 hours, and then the reaction liquor was further stirred at the boiling point (75° C.) for 5 hours, thus o-nitroazobenzene having disappeared to product 2-2-hydroxy-5-methylphenyl)benzotriazole-N-oxide.

Thereafter, water 50 ml was added to the reaction liquor, and the reaction liquor was neutralized to pH 8 with 62% sulfuric acid 16 g to precipitate a crystal. The crystal thus obtained was filtered by suction to separate the crystal, and the separated crystal was fully washed with water and further with methanol. The washed crystal was then dried, thus producing 10.1 g of 2-(2-hydroxy-5-methylphenyl)benzotriazole-N-oxide having a melting point of 138° to 140° C. at the yield of 83.5%.

EXAMPLE 5

2-nitro-2'-hydroxy-5'-methylazobenzene 12.9 g was added to a mixture of methanol 60 ml, water 30 ml and 97% sodium hydroxide 12.4 g, and the resultant mixture was stirred while raising temperature to 65° C. 9-fluorenone 1.2 g and then 90% acetoaldehyde 3.2 g were added to the mixture for 1 hour. The resultant mixture was then heated to the boiling point (75° C.), and was stirred at the boiling point (75° C.) for 6 hours, thus almost all of the azobenzenes having disappeared to produce 2-(2-hydroxy-5-methylphenyl)benzotriazole-N-oxide.

Thereafter, water 50 ml was added to the reaction liquor, and the reaction liquor was neutralized to pH 8 with 62% sulfuric acid 16 g to precipitate a crystal. The crystal thus obtained was filtered by suction, and the separated crystal was fully washed with water and further with methanol. The washed crystal was then dried, thus producing 10.5 g of 2-(2-hydroxy-5-methylphenyl)benzotriazole-N-oxide having a melting point of 138° to 140° C. at the yield of 87.0%.

EXAMPLE 6

2-nitro-2'-hydroxy-5'-methylazobenzene 12.9 g was added to a mixture of methanol 60 ml, water 30 ml and 97% sodium hydroxide 12.4 g, and the resultant mixure was stirred while raising temperature to 65° C. Thereafter, the mixture was cooled to 40° C., and 9-fluorenone 0.8 g and then 80% paraformaldehyde 2.1 g were added to the mixture for 1 hour. The resultant mixture was then heated to the boiling point (75° C.), and was stirred at the boiling point for 6 hours, thus almost all of the azobenzene having disappeared to produce 2-(2-hydroxy-5-methylphenyl)benzotriazole-N-oxide (Process (b) having completed).

In order to conduct Process (c), the reaction liquor was then cooled to 70° C., 9-fluorenone 0.2 g and then 80% paraformaldehyde 2.5 g were added to the reaction liquor for 30 minutes. Thereafter, the reaction liquor was heated to the boiling point (75° C.), and was stirred for futher 4 hours, thus the N-oxide having disappeared to complete Process (c).

Thereafter, water 50 ml was added to the reaction liquor, and the reaction liquor was neutralized to pH 8 with 62% sulfuric acid 16 g to precipitate a crystal. The crystal thus obtained was filtered by suction to separate the crystal, and the appeared crystal was fully washed with water and further with methanol. The washed crystal was then dried, thus producing 9.2 g of 2-(2-hydroxy-5-methylphenyl)benzotriazole having a melting point of 128° to 130° C. at the yield of 81.8%.

EXAMPLE 7

The same procedure as in Example 6 was repeated, except that 2-nitro-2'-hydroxy-5'-methylazobenzene 12.9 g was replaced respectively by (a) 2-nitro-2'-hydroxy-5'-butylazobenzene 14.9 g, (b) 2-nitro-2'-hydroxy-5'-t-octylazobenzene 17.8 g, and (c) 2-nitro-2',4'-dihydroxyazobenzene 14.9 g.

The products thus obtained and their properties are as follows:
(a) 2-(2-hydroxy-5-t-butylphenyl)benzotriazole: Yield: 11.0 g (84.0%), Melting Point: 96.5° to 98.0° C.
(b) 2-(2-hydroxy-5-t-octylphenyl)benzotriazole: Yield: 12.8 g (79.0%), Melting Point: 103° to 105° C.
(c) 2-(2,4-dihydroxyphenyl)benzotriazole: Yield: 9.2 g (70.5%), Melting Point: 187° to 189° C.

EXAMPLE 8

95% potassium hydroxide 17.7 g was added and dissolved in a mixture of ethyl alcohol 80 ml and water 10 ml. 2-nitro-2'-hydroxy-5'-methylazobenzene 12.9 g was then added to the resultant solution at 50° to 60° C. for 30 minutes while stirring, and thereafter 9-fluorenone 0.6 g and 35% formalin 5.6 g were added to the solution in 30 minutes. The resultant mixture was stirred for 1 hour at 65° to 70° C., and was further reacted at the boiling point (85° C.) for 4 hours, thus almost all of the azobenzene having disappeared to complete the reaction of Process (b). Anthrone 0.4 g and 35% formalin 6.4 g were then added to the reaction liquor by dropwise for 30 minutes, and the reaction liquor was further reacted for 8 hours while stirring, thus the intermediate product of Process (b) having disappeared to complete the reaction of Process (c).

Thereafter, water 50 ml was added to the reaction liquor, and the reaction liquor was neutralized to pH 8 with 62% sulfuric acid 16 g to precipitate a crystal. The crystal thus obtained was filtered by suction to separate the crystal, and the separated crystal was fully washed with water and further with ethyl alcohol. The washed crystal was then dried, thus producing 8.7 g of 2-(2-hydroxy-5-methylphenyl)benzotriazole-N-oxide having a melting point of 138° to 140° C. at the yield of 77.3%.

EXAMPLE 9

Methanol 60 ml, water 30 ml, 97% sodium hydroxide 12.4 g, and 2-nitro-2'-hydroxy-5'-methylazobenzene 12.9 g were mixed and stirred. After adding benzanthrone 1.2 g to the resultant mixture at 65° to 70° C., 80% paraformaldehyde 4.6 g was added to the mixture for 2 hours, and then the reaction liquor was further stirred at the boiling point (75° C.) for 5 hours, thus o-nitroazobenzene having disappeared to produce 2-(2-hydroxy-5-methylphenyl)benzotriazole-N-oxide (Process (b) having completed). In order to conduct Process (c), the reaction liquor was further stirred for 6 hours, thus the N-oxide having disappeared to complete Process (c).

Thereafter, water 50 ml was added to the reaction liquor, and the reaction liquor was neutralized to pH 8 with 62% sulfuric acid 16 g to precipitate a crystal. The crystal thus obtained was filtered by suction to separate the crystal, and the separated crystal was fully washed with water and further with methanol. The washed crystal was then dried, thus producing 8.4 g of 2-(2-hydroxy-5-methylphenyl)benzotriazole having a melting point of 128° to 130° C. at the yield of 74.7%.

EXAMPLE 10

2-nitro-2'-hydroxy-5'-methylazobenzene 12.9 g was added to a mixture of methanol 60 ml, water 30 ml and 97% sodium hydroxide 12.4 g, and the resultant mixture was stirred while raising temperature to 65° C. 9-fluorenone 1.2 g and then 90% acetoaldehyde 6.5 g were added to the mixture for 1 hour. The resultant mixture was then stirred at the boiling point (75° C.) for 6 hours, thus almost all of the azobenzene having disappeared to produce 2-(2-hydroxy-5-methylphenyl)benzotriazole-N-oxide (Process (b) having completed). In order to conduct Process (c), the reaction liquor was further stirred at the boiling point for 5 hours, thus the N-oxide having disappeared to complete Process (c).

Thereafter, water 50 ml was added to the reaction liquor, and the reaction liquor was neutralized to pH 8 with 62% sulfuric acid 16 g to precipitate a crystal. The crystal thus obtained was filtered by suction to separate the crystal, and the separated crystal was fully washed with water and further with methanol. The washed crystal was then dried, thus producing 9.1 g of 2-(2-hydroxy-5-methylphenyl)benzotriazole having a melting point of 128° to 130° C. at the yield of 80.9%.

EXAMPLE 11

Methanol 110 ml, water 20 ml, 97% sodium hydroxide 12.4 g, and 2-nitro-2'-hydroxy-5'-t-octylazobenzene 17.8 g were mixed and stirred. After adding 9-fluorenone 2.4 g to the resultant mixture at 65° to 70° C., 80% paraformaldehyde 6 g was added to the mixture for 4 hours, and then the reaction liquor was further stirred at the boiling point (73° C.) for 6 hours, thus the reduction reaction having completed.

Thereafter, water 50 ml was added to the reaction liquor, and the reaction liquor was neutralized to pH 8 with 62% sulfuric acid 16 g to precipitate a crystal. The crystal thus obtained was filtered by suction to separate the crystal, and the separated crystal was fully washed with water and further with methanol. The washed crystal was then dried, thus producing 13.1 g of 2-(2-hydroxy-5-t-octylphenyl)benzotriazole having a melting point of 103° to 105° C. at the yield of 81.0%.

EXAMPLE 12

2-(2-hydroxy-3-t-butyl-5-methylphenyl)-5-chlorobenzotriazole-N-oxide 16.6 g was added to a mixture of methanol 72 ml, water 20 ml and 97% sodium hydroxide 12.4 g, and the resultant mixture was stirred at 70° C. for 30 minutes, then having been cooled to 65° C. After adding 9-fluorenone 0.8 g to the resultant mixture, 80% paraformaldehyde 2.5 g was added to the mixture for 30 minutes, and the resultant mixture was stirred at 60° to 70° C. for 1 hour, and further at the boiling point (73° C.) for 4 hours, thus 2-(2-hydroxy-3-t-butyl-5-methylphenyl)-5-chlorobenzotriazole-N-oxide having disappeared to complete the reduction reaction.

Thereafter, water 50 ml was added to the reaction liquor by dropwise at 65° to 70° C., and then reaction liquor was neutralized with 62.5% sulfuric acid 12 g to precipitate a crystal. The crystal thus obtained was filtered by suction to separate the crystal, and the separated crystal was fully washed with water and further with methanol. The washed crystal was then dried, thus producing 14.7 g of 2-(2-hydroxy-3-t-butyl-5-methylphenyl)-5-chlorobenzotriazole having a melting point of 138° to 140° C. at the yield of 93.0%.

EXAMPLE 13

The same procedure as in Example 12 was repeated, excepted that 2-(2-hydroxy-3-t-butyl-5-methylphenyl)-5-chlorobenzotriazole-N-oxide 16.6 g was replaced respectively by (a) 2-(2-hydroxy-3,5-di-t-butylphenyl)-5-chlorobenzotriazole-N-oxide 19.5 g, (b) 2-(2-hydroxy-3,5-di-t-butylphenyl)benzotriazole-N-oxide 17.8 g, and (c) 2-(2-hydroxy-3,5-di-t-amylphenyl)benzotriazole-N-oxide 19.2 g.

The products thus obtained and their properties are as follows:
(a) 2-(2-hydroxy-3,5-di-t-butylphenyl)-5-chlorobenzotriazole: Yield: 16.1 g (90.0%), Melting Point: 154° to 155.5° C.
(b) 2-(2-hydroxy-3,5-di-t-butylphenyl)benzotriazole: Yield: 14.8 g (91.5%), Melting Point: 150° to 152° C.

(c) 2-(2-hydroxy-3,5-di-t-amylphenyl)benzotriazole:
Yield: 15.4 g (88.0%), Melting Point: 77° to 79° C.

EXAMPLE 14

2-(2-hydroxy-3-t-butyl-5-methylphenyl)-5-chlorobenzotriazole-N-oxide 16.6 g was added to a mixture of ethyl alcohol 80 ml, water 10 ml and 95% potassium hydroxide 17.7 g, and the resultant mixture was stirred at 80° C. for 30 minutes, then having been cooled to 65° C. After adding anthrone 1.4 g to the resultant mixture, 35% formalin 6.5 g was added to the mixture by dropwise for 30 minutes, and the resultant mixture was stirred at 65° to 70° C. for 1 hour, and further at the boiling point (87° C.) for 10 hours, thus 2-(2-hydroxy-3-t-butyl-5-methylphenyl)-5-chlorobenotriazole-N-oxide having disappeared to complete the reduction reaction.

Thereafter, water 50 ml was slowly added to the reaction liquor, and the reaction liquor was neutralized with 62.5% sulfuric acid 12 g to precipitate a crystal. The crystal thus obtained was filtered by suction to separate the crystal, and the separated crystal was fully washed with water and further with ethyl alcohol. The washed crystal was then dried, thus producing 14.5 g of 2-(2-hydroxy-3-t-butyl-5-methylphenyl)-5-chlorobenzotriazole having a melting point of 138° to 140° C. at the yield of 92.0%.

EXAMPLE 15

2-(2-hydroxy-3,5-di-t-butylphenyl)-5-chlorobenzotriazole-N-oxide 18.7 g was added to a mixture of methanol 80 ml, water 30 ml and 97% sodium hydroxide 12.4 g, and the resultant mixture was stirred at 70° C. for 30 minutes, then having been cooled to 60° C. After adding benzanthrone 1.2 g to the resultant mixture, 90% acetoaldehyde 3.2 g was added to the mixture by dropwise for 30 minutes, and the resultant mixture was stirred at 60° to 70° C. for 30 minutes, and further at the boiling point (74° C.) for 4 hours, thus 2-(2-hydroxy-3,5-di-t-butylphenyl)-5-chlorobenzotriazole-N-oxide having disappeared to complete the reduction reaction.

Thereafter, water 50 ml was added to the reaction liquor by dropwise at 65° to 70° C., and the reaction liquor was neutralized with 62.5% sulfuric acid 12 g to precipitate a crystal. The crystal thus obtained was filtered by suction to separate the crystal, and the separated crystal was fully washed with water and further with methanol. The washed crystal was then dried, thus producing 15.9 g of 2-(2-hydroxy-3,5-di-t-butylphenyl)-5-chlorobenzotriazole having a melting point of 154° to 155.5° C. at the yield of 89.0%.

EXAMPLE 16

2-(2-hydroxy-5-methylphenyl)benzotriazole-N-oxide 10.7 g was added to a mixture of methanol 60 ml, water 30 ml and 97% sodium hydroxide 12.4 g, and the resultant mixture was heated to 70° C. After adding 9-fluorenone 1.0 g to the resultant mixture, 80% paraformaldehyde 2.5 g was added to the mixture for 30 minutes, and the resultant mixture was heated to the boiling point (75° C.). The resultant mixture was further stirred at the boiling point for 4 hours, thus 2-(2-hydroxy-5-methylphenyl)benzotriazole-N-oxide having disappeared to complete the reduction reaction.

Thereafter, water 50 ml was added to the reaction liquor, and the reaction liquor was neutralized with 62% sulfuric acid 16 g to precipitate a crystal. The crystal thus obtained was filtered by suction to separate the crystal, and the separated crystal was fully washed with water and further with methanol. The washed crystal was then dried, thus producing 9.2 g of 2-(2-hydroxy-5-methylphenyl)benzotriazole having a melting point of 129° to 130° C. at the yield of 92.1%.

What I claim is:

1. A method for preparing a 2-phenylbenzotriazole of formula I,

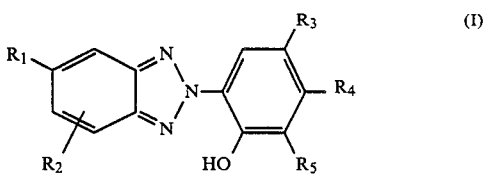

wherein $R_1$ represents a hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkoxyl group having a carbon number of 1 to 4; $R_3$ represents hydrogen or chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents a hydrogen or chlorine atom, hydroxyl group, or a lower alkoxyl group having a carbon number of 1 to 4; and $R_5$ represents a hydrogen atom, an alkyl group having a carbon number of 1 to 12, or a phenylalkyl group, the alkyl part of which has a carbon number of 1 to 4, which comprises reducing an o-nitroazobenzene of formula III,

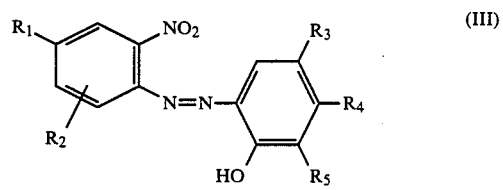

wherein $R_1$, $R_2$, $R_3$, $R_4$ and $R_5$ are as defined above with an aldehyde reducing agent wherein said reducing aldehyde is selected from the group consisting of formaldehyde, paraformaldehyde and acetoaldehyde, and wherein said reducing reaction is carried out in the presence of a mono-oxo aromatic ketone catalyst selected from the group consisting of benzanthrone, anthrone and 9-fluorenone and a base in a water based solvent.

2. A method as claimed in claim 1, wherein 2 to 4 mole aldehyde are used per mole o-nitroazobenzene of formula III.

3. A method as claimed in claim 1, wherein, in the first of two steps, 1 to 2 mole aldehyde are used per mole o-nitroazobenzene of formula III, to give an intermediate which is a 2-phenylbenzotriazole-N-oxide of formula II,

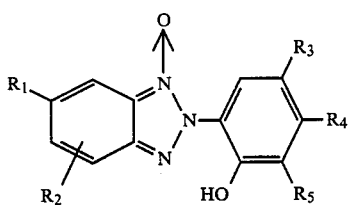

(II)

(wherein $R_1$, $R_2$, $R_3$, $R_4$ and $R_5$ are as defined in claim 1) and, in the second step, 1 to 4 mole aldehyde are used per mole intermediate of formula II.

4. A method for preparing a 2-phenylbenzotriazole of formula I as defined in claim 1, which comprises reducing 1 mole 2-phenylbenzotriazole-N-oxide of formula II as defined in claim 3 with 1 to 4 mole aldehyde in the presence of an aromatic ketone catalyst and base.

5. A method for preparing a 2-phenylbenzotriazole-N-oxide of formula II as defined in claim 3, which comprises reducing 1 mole o-nitroazobenzene of formula III as defined in claim 1 with 1 to 2 mole aldehyde in the presence of an aromatic ketone catalyst and base.

6. The method of claim 1 wherein said aromatic ketone catalyst is used in an amount of 0.2 to 30% by weight, based on the weight of the starting material of formula II and III.

7. The method of claim 1 wherein said base is sodium hydroxide or potassium hydroxide in an amount of 1 to 12 moles per mole of starting material of formula II or III.

* * * * *